(12) United States Patent
Mahajan et al.

(10) Patent No.: US 10,702,167 B2
(45) Date of Patent: Jul. 7, 2020

(54) METHOD TO TRIGGER STORAGE OF ONSET OF PHYSIOLOGIC CONDITION IN AN IMPLANTABLE DEVICE

(71) Applicant: Cardiac Pacemakers, Inc., St. Paul, MN (US)

(72) Inventors: Deepa Mahajan, Roseville, MN (US); David L. Perschbacher, Coon Rapids, MN (US); Arjun D. Sharma, St. Paul, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 407 days.

(21) Appl. No.: 15/427,602

(22) Filed: Feb. 8, 2017

(65) Prior Publication Data

US 2017/0231505 A1 Aug. 17, 2017

Related U.S. Application Data

(60) Provisional application No. 62/309,258, filed on Mar. 16, 2016, provisional application No. 62/294,577, filed on Feb. 12, 2016.

(51) Int. Cl.
*A61B 5/0205* (2006.01)
*A61B 5/046* (2006.01)
(Continued)

(52) U.S. Cl.
CPC .......... *A61B 5/0205* (2013.01); *A61B 5/0022* (2013.01); *A61B 5/021* (2013.01);
(Continued)

(58) Field of Classification Search
CPC ............... A61N 1/3987; A61N 1/3956; A61N 1/36507; A61N 1/3624; A61B 5/0205;
(Continued)

(56) References Cited

U.S. PATENT DOCUMENTS 4,250,888 A * 2/1981 Grosskopf ........... A61B 5/0245
600/515
5,313,953 A * 5/1994 Yomtov ............... A61B 5/0031
600/381
(Continued)

FOREIGN PATENT DOCUMENTS

CN 108601941 A 9/2018
EP 0554208 A2 8/1993
(Continued)

OTHER PUBLICATIONS

Hongo, Richard H., et al., "Evaluating Patients with Unexplained Syncope", Cardiovasc Rev Rep. 2004; 25(5), (2004), 1-8.
(Continued)

*Primary Examiner* — David J. McCrosky
(74) *Attorney, Agent, or Firm* — Schwegman Lundberg & Woessner, P.A.

(57) ABSTRACT

An apparatus includes a sensing circuit configured to generate a sensed physiological signal that includes physiological information of a subject, a detection circuit, and a control circuit. The detection circuit detects a physiological condition of a subject using the physiological signal. The control circuit stores sampled values of a segment of the physiological signal in temporary memory storage; and stores the sampled values in non-temporary storage in response to receiving an indication of continued detection of the physiological condition.

19 Claims, 8 Drawing Sheets

(51) Int. Cl.

| | |
|---|---|
| *A61B 5/0215* | (2006.01) |
| *A61B 5/08* | (2006.01) |
| *A61B 5/0456* | (2006.01) |
| *A61B 5/00* | (2006.01) |
| *G16H 40/67* | (2018.01) |
| *A61B 5/021* | (2006.01) |
| *A61B 5/0245* | (2006.01) |
| *A61B 5/11* | (2006.01) |
| *A61B 7/02* | (2006.01) |
| *A61N 1/362* | (2006.01) |
| *A61N 1/365* | (2006.01) |
| *A61N 1/39* | (2006.01) |
| *A61B 5/042* | (2006.01) |

(52) U.S. Cl.
CPC .......... *A61B 5/0215* (2013.01); *A61B 5/0245* (2013.01); *A61B 5/046* (2013.01); *A61B 5/0456* (2013.01); *A61B 5/08* (2013.01); *A61B 5/0816* (2013.01); *A61B 5/1117* (2013.01); *A61B 5/686* (2013.01); *A61B 5/6869* (2013.01); *A61B 5/7282* (2013.01); *A61B 5/7285* (2013.01); *A61B 7/02* (2013.01); *A61N 1/3624* (2013.01); *A61N 1/36507* (2013.01); *A61N 1/3956* (2013.01); *A61N 1/3987* (2013.01); *G16H 40/67* (2018.01); *A61B 5/0024* (2013.01); *A61B 5/0031* (2013.01); *A61B 5/0422* (2013.01); *A61B 5/7246* (2013.01)

(58) Field of Classification Search
CPC ..... A61B 5/6869; A61B 5/7285; A61B 5/046; A61B 5/0245; A61B 5/0022; A61B 5/7282; A61B 5/0456; A61B 5/021; A61B 5/0215; A61B 5/08; A61B 5/686; A61B 5/0816; A61B 5/7246; A61B 5/0031; A61B 5/0464; A61B 5/0468; A61B 5/0472

See application file for complete search history.

(56) References Cited

U.S. PATENT DOCUMENTS

| | | | |
|---|---|---|---|
| 5,411,031 A | 5/1995 | Yomtov | |
| 6,041,251 A * | 3/2000 | Kim | A61B 5/046 |
| | | | 600/518 |
| 6,076,015 A | 6/2000 | Hartley et al. | |
| 6,719,701 B2 | 4/2004 | Lade | |
| 7,115,096 B2 | 10/2006 | Siejko et al. | |
| 7,566,308 B2 | 7/2009 | Stahmann | |
| 7,634,310 B2 * | 12/2009 | Lee | A61B 5/02405 |
| | | | 600/509 |
| 7,904,142 B2 | 3/2011 | Kim et al. | |
| 8,366,641 B2 | 2/2013 | Wang et al. | |
| 8,929,981 B2 * | 1/2015 | Perschbacher | A61N 1/36585 |
| | | | 607/18 |
| 10,213,125 B2 * | 2/2019 | Cao | A61B 5/0456 |
| 2008/0091239 A1 * | 4/2008 | Johansson | A61N 1/36514 |
| | | | 607/4 |

FOREIGN PATENT DOCUMENTS

| | | |
|---|---|---|
| EP | 0978253 A2 | 2/2000 |
| EP | 0757577 B1 | 1/2004 |
| WO | WO-2012050908 A2 | 4/2012 |
| WO | WO-2017139340 A1 | 8/2017 |

OTHER PUBLICATIONS

"European Application Serial No. 17706073.8, Response filed Apr. 4, 2019 to Communication Pursuant to Rules 161 & 162 dated Oct. 8, 2018", 18 pgs.

"International Application Serial No. PCT/US2017/016952, International Preliminary Report on Patentability dated Aug. 23, 2018", 8 pgs.

"International Application Serial No. PCT/US2017/016952, International Search Report dated Apr. 24, 2017", 5 pgs.

"International Application Serial No. PCT/US2017/016952, Written Opinion dated Apr. 24, 2017", 3 pgs.

* cited by examiner

METHOD TO TRIGGER STORAGE OF ONSET OF PHYSIOLOGIC CONDITION IN AN IMPLANTABLE DEVICE

CLAIM OF PRIORITY

This application claims the benefit of priority under 35 U.S.C. § 119(e) of U.S. Provisional Patent Application Ser. No. 62/309,258, filed on Mar. 16, 2016, and U.S. Provisional Patent Application Ser. No. 62/294,577, filed on Feb. 12, 2016, each of which is herein incorporated by reference in its entirety.

BACKGROUND

Ambulatory medical devices include implantable medical devices (IMDs), wearable medical devices, handheld medical devices, and other medical devices.

Some examples of IMDs include cardiac function management (CFM) devices such as implantable pacemakers, implantable cardioverter defibrillators (ICDs), subcutaneous implantable cardioverter defibrillators (S-ICDs), cardiac resynchronization therapy devices (CRTs), and devices that include a combination of such capabilities. The devices can be used to treat patients or subjects using electrical or other therapy, or to aid a physician or caregiver in patient diagnosis through internal monitoring of a patient's condition.

Some implantable medical devices can be diagnostic-only devices, such as implantable loop recorders (ILRs) and subcutaneously implantable heart failure monitors (SubQ HFMs). The devices may include electrodes in communication with one or more sense amplifiers to monitor electrical heart activity within a patient, or can include one or more sensors to monitor one or more other internal patient parameters. Subcutaneously implantable devices may include electrodes that are able to sense cardiac signals without being in direct contact with the patient's heart. Other examples of IMDs include implantable drug delivery systems or implantable devices with neural stimulation capability (e.g., vagus nerve stimulator, baroreflex stimulator, carotid sinus stimulator, spinal cord stimulator, deep brain stimulator, etc.).

Some examples of wearable medical devices include wearable cardioverter defibrillators (WCDs) and wearable diagnostic devices (e.g., an ambulatory monitoring vest, holter monitor, cardiac event monitor, or mobile cardiac telemetry devices). WCDs can be monitoring devices that include surface electrodes. The surface electrodes may be arranged to provide one or both of monitoring to provide surface electrocardiograms (ECGs) and delivery of cardioverter and defibrillator shock therapy. In some examples, a wearable medical device can also include a monitoring patch worn by the patient such as an adherable patch or can be included with an article of clothing worn by the patient.

Some examples of handheld medical devices include personal data assistants (PDAs) and smartphones. The handheld devices can be diagnostic devices that record an electrocardiograph (ECG) or other physiological parameter while the device is resting in the patient's hand or being held to the patient's chest.

CFM devices can be used to record information related to cardiac events experienced by the patient. These recorded episodes can be uploaded from the CFM device and evaluated by a clinician. These recordings can be used to monitor the progression of disease by the patient. However, by the time a physiological condition is detected, the onset of condition may have already passed and useful information regarding the onset of the condition is not present in the recording. Knowledge regarding the onset of a physiological condition can be useful to physicians and clinicians for diagnostic purposes or to tailor performance of a medical device to that patient's needs to provide the most effective patient therapy.

Overview

It can be desirable for ambulatory medical devices to correctly detect and identify cardiac events or to collect information used to identify cardiac events. This can help to provide the most effective device-based therapy or non-device based therapy for the patient. The present subject matter relates to improving recording of cardiac events.

One example apparatus of the present subject matter can include a sensing circuit configured to generate a sensed physiological signal that includes physiological information of a subject, a detection circuit, and a control circuit. The detection circuit detects onset of a physiological condition of a subject using the physiological signal. The control circuit stores sampled values of a segment of the physiological signal in temporary memory storage; and stores the sampled values in non-temporary storage in response to receiving an indication of confirmation of the physiological condition.

This section is intended to provide a brief overview of subject matter of the present patent application. It is not intended to provide an exclusive or exhaustive explanation of the invention. The detailed description is included to provide further information about the present patent application such as a discussion of the dependent claims and the interrelation of the dependent and independent claims in addition to the statements made in this section.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An ambulatory medical device can include one or more of the features, structures, methods, or combinations thereof described herein. For example, a cardiac monitor or a cardiac stimulator may be implemented to include one or more of the advantageous features or processes described below. It is intended that such a monitor, stimulator, or other ambulatory device need not include all of the features described herein, but may be implemented to include selected features that provide for unique structures or functionality. Such a device may be implemented to provide a variety of therapeutic or diagnostic functions.

Figure 1:
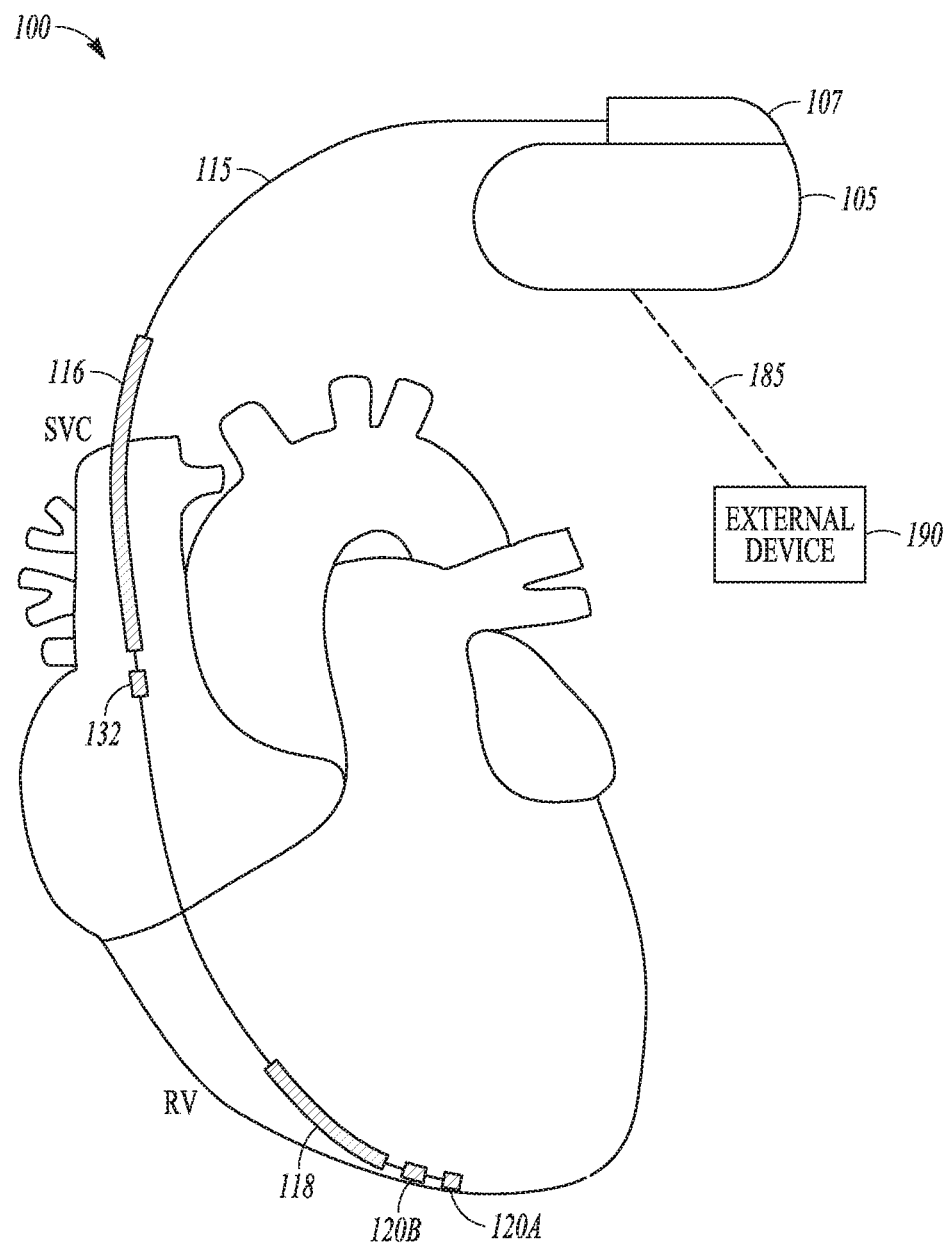
FIG. 1 is an illustration of an example of portions of a medical device system that includes an IMD.

FIG. 1 is an illustration of an example of portions of a system 100 that includes an ambulatory medical device that is an IMD 105. Examples of the IMD 105 include, without limitation, a pacemaker, a cardioverter, a defibrillator, and other cardiac monitoring and therapy delivery devices, including cardiac devices that include or work in coordination with one or more neuro-stimulating devices, drugs, drug delivery systems, or other therapies. In an example, the system 100 shown is used to treat a cardiac arrhythmia. The IMD 105 typically includes an electronics unit coupled by one or more cardiac leads 115 to a heart of a patient or subject. The electronics unit of the IMD 105 typically includes components that are enclosed in a hermetically-sealed housing sometimes referred to as a canister or "can." The system 100 also typically includes an IMD programmer or other external system 190 that communicates one or more wireless signals 185 with the IMD 105, such as by using radio frequency (RF) or by one or more other telemetry methods.

The example shown includes a right ventricular (RV) lead 115 having a proximal end and a distal end. The proximal end is coupled to a header connector 107. The distal end is configured for placement in the RV. The RV lead 115 can include one or more of a proximal defibrillation electrode 116, a distal defibrillation electrode 118 (e.g., RV Coil), an RV tip electrode 120A, and an RV ring electrode 120B. The defibrillation electrode 116 is generally incorporated into the lead body such as in a location suitable for supraventricular placement in the superior vena cava (e.g., SVC Coil). In some examples, the RV lead 115 includes a ring electrode 132 (e.g., SVC ring) in the vicinity of the proximal defibrillation electrode 116. The defibrillation electrode 118 is incorporated into the lead body near the distal end, such as for placement in the RV. The RV electrodes 120A and 120B can form a bipolar electrode pair and are generally incorporated into the lead body at the lead distal end. The electrodes 116, 118, 120A, and 120B are each electrically coupled to IMD 105, such as through one or more conductors extending within the lead body. The proximal defibrillation electrode 116, distal defibrillation electrode 118, or an electrode formed on the can of IMD 105 allow for delivery of cardioversion or defibrillation pulses to the heart. The RV tip electrode 120A, RV ring electrode 120B, or an electrode formed on the can of IMD 105 allow for sensing an RV electrogram signal representative of RV depolarizations and delivering RV pacing pulses. The IMD 105 includes a sense amplifier circuit to provide amplification or filtering of the sensed signal. Sensing and pacing allows the IMD 105 to adjust timing of the heart chamber contractions.

Some IMDs, such as shown in FIG. 1, may not include any electrodes for sensing electrical activity in an atrium. For example, the IMD 105 can be an ICD with single ventricular chamber sensing. The ICD can include an electrode attached to a single ventricular lead, and use intrinsic cardiac signals sensed with the ventricular electrode for arrhythmia detection and discrimination (e.g., by rate sensing and/or depolarization signal morphology analysis).

An IMD may be a diagnostic-only device and not provide electrical therapy to the patient. Such a device may include a combination of the RV tip electrode 120A, RV ring electrode 120B, or the electrode formed on the can of IMD 105 allow for sensing ventricular depolarizations. Note that the specific arrangement of leads and electrodes are shown the illustrated example of FIG. 1 is intended to be non-limiting.

Figure 2:
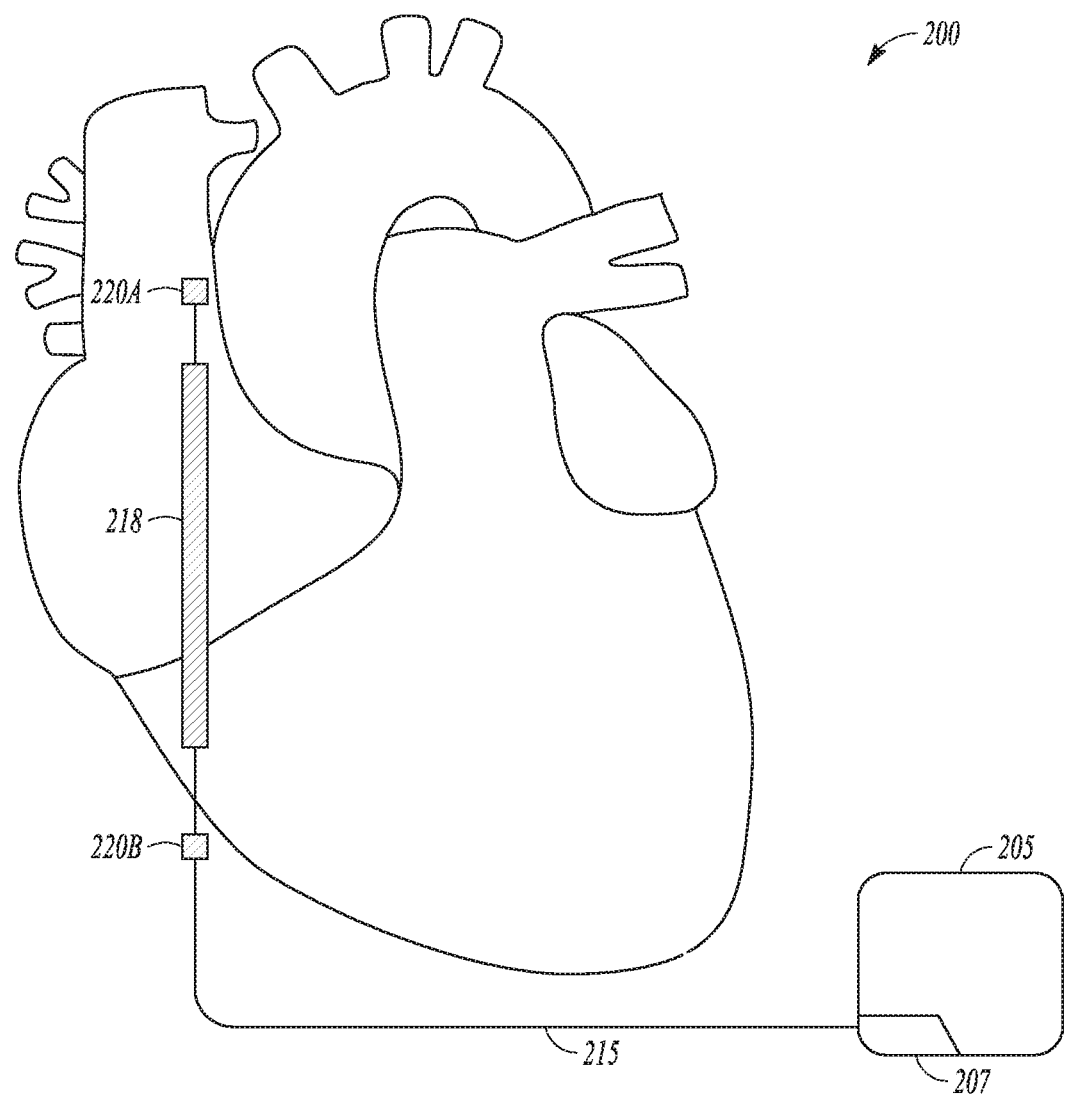
FIGS. 2 and 3 are illustrations of further examples of an IMD.

FIG. 2 is an illustration of another example of portions of a system 200 that includes an ambulatory medical device that is an S-ICD 205. The S-ICD 205 is implantable subcutaneously and includes a lead 215. The lead 215 is also implanted subcutaneously and the proximal end of the lead 215 is coupled to a header connector 207. The lead 215 can include electrode 220A and electrode 220B to sense ventricular depolarization (e.g., using far-field sensing), but in the example illustrated the lead does not include any electrodes that directly contact the heart. The lead 215 includes a defibrillation electrode 218 that may be a coil electrode. The S-ICD 205 may provide one or more of cardioversion therapy and defibrillation high energy shock therapy to the heart using the defibrillation electrode 218 and an electrode formed on the can of the S-ICD 205. In some examples, the S-ICD 205 may also provide pacing pulses for anti-tachycardia therapy or bradycardia therapy. Note that direct atrial sensing is not provided in the arrangement of the electrodes, but electrodes 220A and 220B allow for sensing a far-field ventricular electrogram signal.

Figure 3:
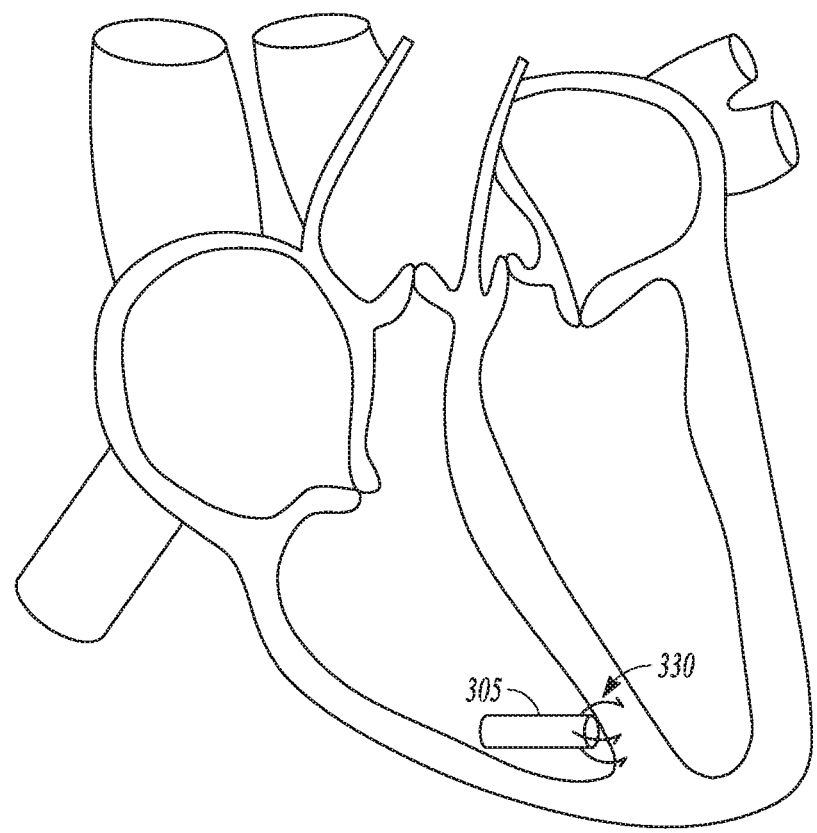

FIG. 3 is an illustration of an example of an IMD that is leadless. In the example shown, the IMD is a leadless pacemaker 305. The leadless pacemaker 305 is shown positioned at the endocardium within a ventricular chamber, but the leadless pacemaker 305 may be positioned at other locations of the heart. The leadless pacemaker 305 example has a cylindrical or bullet shape housing and may include one or more electrodes arranged along the cylindrical housing to sense electrical signals of the heart and/or provide electrical stimulation for pacing the heart. The one or more electrodes may be used for communication. The leadless pacemaker 305 may include a mechanism 330 to fix the pacemaker to the myocardium. Examples of the fixation mechanism can include one or more tines, one or more barbed tines, and one or more helix-shaped fixation mechanisms. Direct atrial sensing may not be provided by the electrodes for the device placement shown in the example, but the electrodes may provide an RV electrogram signal.

Other examples of an ambulatory medical devices include an implantable loop recorder (ILR), a neurostimulator (including but not limited to vagus nerve stimulators, baroreceptor stimulators, and spinal cord stimulators), or other IMD. These types of devices may not include an electrode positioned in the atrium. An ambulatory medical device may be a diagnostic-only device without leads in the heart and may include one or more hemodynamic sensors such as a respiration sensor, blood pressure sensor, or heart sound sensor. A diagnostic-only device may include a posture sensor or a physical activity sensor.

Figure 4:
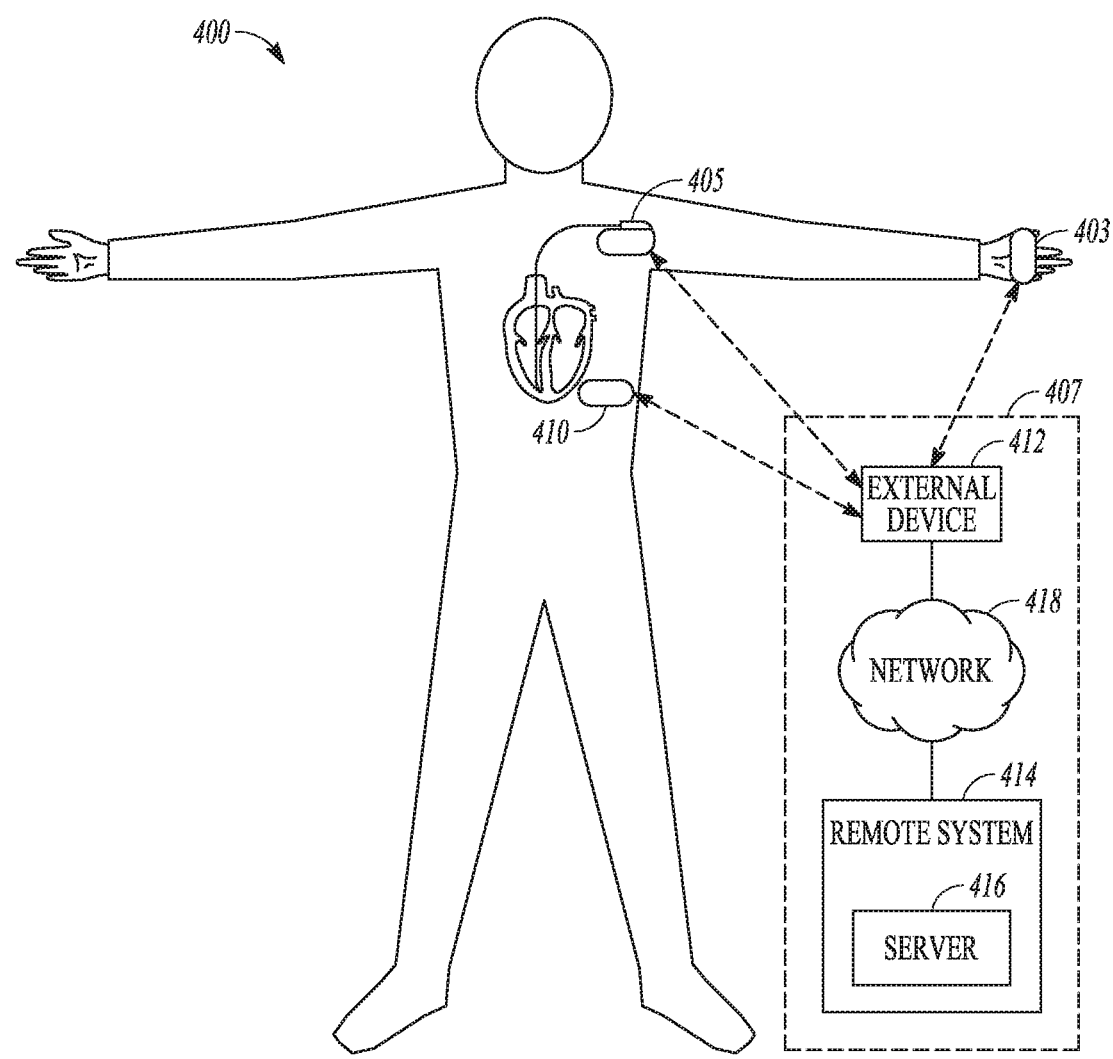
FIG. 4 is an illustration of portions of another example of a medical device system.

FIG. 4 is an illustration of portions of another example of a medical device system 400. The system 400 may include one or more ambulatory medical devices, such as a conventionally implantable or subcutaneously implantable medical device 405, a wearable medical device 410, or a handheld medical device 403. One or more of the medical devices can include a communication circuit (e.g., a telemetry circuit) to communicate device determined information to a communication system 407. The communication system 407 can include an external communication device 412 and a remote system 414 that communicates with the external communication device 412 via a network 418 (e.g., the internet, a proprietary computer network, or a cellular phone network). The remote system 414 may include a server 416 remotely located from the external communication device 412 and the subject to perform patient management functions. The external communication device 412 may include a programmer to program therapy parameters of a device-based therapy provided by the implantable medical device. One or both of the external communication device 412 and the remote system 414 may include a display to present the information to a user, such as a clinician.

As explained previously some ambulatory medical devices can be used to record signals produced by sensors included in the devices. These recorded signals can provide useful information that can be evaluated by a clinician to monitor the progression of a patient's disease, such as heart failure (HF) for example. However, by the time a physiological condition is detected, the onset portion of the condition may have already passed by the time the storage of signals is triggered. Useful information regarding the onset of the condition is not captured in the recording and valuable information may not be captured in the recorded signals.

Figure 5:
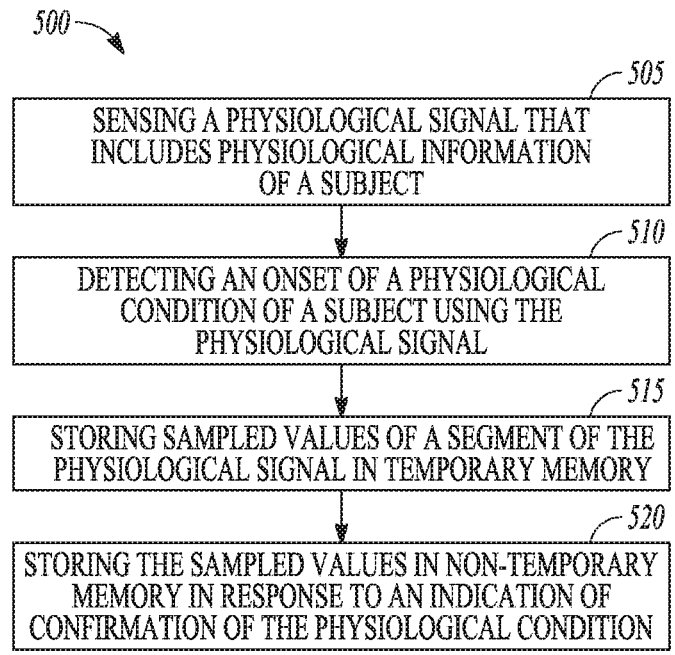
FIG. 5 shows a flow diagram of an example of a method of operating an ambulatory medical device.

FIG. 5 is a flow diagram of a method of controlling operation of an ambulatory medical device to trigger storage of one or more physiological signals in response to detection of a physiological condition of a patient or subject. At 505, a physiological signal is sensed using a sensing circuit of the medical device. The physiological signal includes physiological information of a subject.

At 510, an onset of a physiological condition of a subject is detected by the medical device using the physiological signal. Some examples of the physiological condition include atrial fibrillation (AF) and syncope.

At 515, sampled values of a segment of the physiological signal is stored in temporary memory storage. The storage may be temporary because the ambulatory medical device may overwrite the temporary storage as the storage is filled. In some examples, the ambulatory medical device stores the signal segment recurrently or periodically. In some examples, the ambulatory medical device initiates or triggers storage of the signal segment in response to detection of onset of the physiological condition. At 520, the sampled values are stored in non-temporary storage in response to an indication of continued detection of the physiological condition or a confirmation of the physiological condition.

Figure 6:
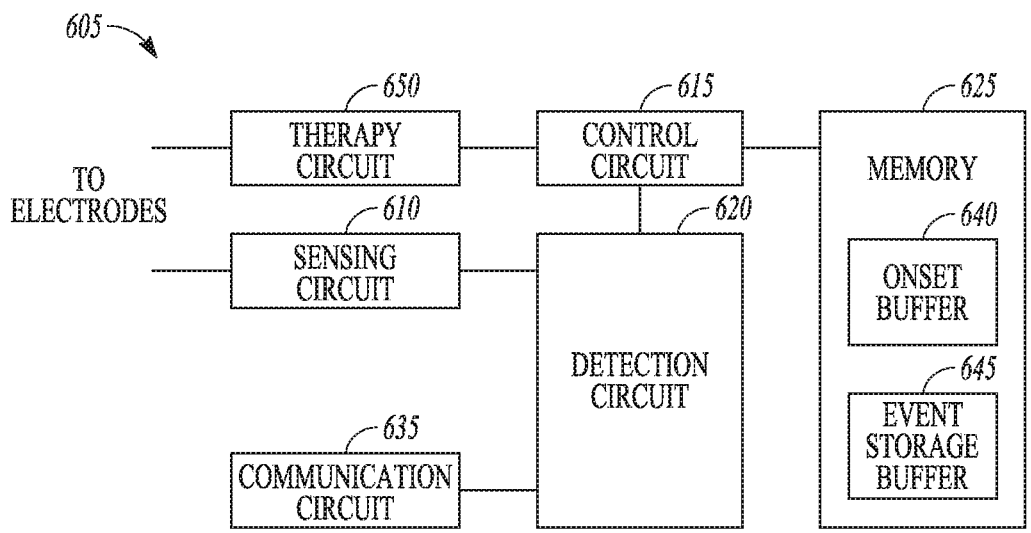
FIG. 6 shows a block diagram of portions of an example of an ambulatory medical device.

FIG. 6 shows a block diagram of portions of an example of an ambulatory medical device 605. The device 605 includes one or more sensing circuits 610, a control circuit 615, a detection circuit 620, and may include a memory 625. The sensing circuit 610 may generate a sensed physiological signal that includes physiological information of a subject. In certain examples, the sensing circuit 610 may be electrically coupled to one or more implantable electrodes included in a lead arranged for placement in a heart chamber. In certain examples, the sensing circuit 610 may be electrically coupled to one or more implantable electrodes included in a leadless implantable medical device. In certain examples, the sensing circuit 610 may be a cardiac signal sensing circuit and can be electrically coupled to one or more implantable electrodes configured to sense cardiac signals without direct cardiac contact with the subject (e.g., a subcutaneously implantable electrode).

In some examples, the sensing circuit generates a signal representative of physiological impedance. For instance, an electrical current could be applied between an RV electrode (e.g., RV electrode 120B in FIG. 1) and an electrode formed on the device can. Voltage resulting from the applied current can be measured using another RV electrode (e.g., electrode 118) and an electrode formed on the device header 107. Impedance across at least a portion of the thorax region of the subject may then be calculated using Ohms Law. The signal representative of physiological impedance can vary with respiration of the subject to provide respiration information. The impedance sensing circuit can therefore be used as a respiration sensor to measure respiration parameters such as respiratory rate, tidal volume, minute respiration volume, and derived parameters such as the ratio of respiratory rate over tidal volume. An approach to monitoring thoracic impedance is described in Hartley et al., U.S. Pat. No. 6,076,015, "Rate Adaptive Cardiac Rhythm Management Device Using Transthoracic Impedance," filed Feb. 27, 1998, which is incorporated herein by reference in its entirety.

In some examples, the sensing circuit 610 includes a pulmonary arterial pressure (PAP) sensing circuit. A PAP sensing circuit may be implanted in a pulmonary artery to generate a PAP signal. Examples of an implantable PAP sensor are described in U.S. Pat. No. 7,566,308, titled "Method and Apparatus for Pulmonary Artery Pressure Signal Isolation," filed on Oct. 13, 2005, which is incorporated herein by reference in its entirety.

In some examples, the sensing circuit 610 includes a heart sound sensing circuit. Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the beginning of diastole. The third heart sound (S3) and fourth heart sound (S4) are related to filling pressures of the left ventricle during diastole.

The physiological signal can be a heart sound signal representative of one or more heart sounds produced by the heart sound sensor circuit. An example of a heart sound sensing circuit includes an accelerometer or microphone. An approach for measuring heart sounds can be found in U.S. Pat. No. 7,115,096, titled "Method and Apparatus for Monitoring of Diastolic Hemodynamics," filed on Dec. 30, 2002, which is incorporated herein by reference in its entirety.

In some examples, the sensing circuit 610 includes a posture sensing circuit that generates a posture signal representative of posture of the subject. An example of a posture sensing circuit includes an accelerometer. An approach for determining patient posture using a multi-dimensional posture sensor can be found in Wang et al., "Posture Detector Calibration and Use," U.S. Pat. No. 8,366,641, filed Nov. 18, 2005, which is incorporated herein by reference in its entirety.

In some examples, the sensing circuit 610 includes a physical activity sensing circuit that generates an activity signal representative of physical activity of the subject. An example of a physical activity sensing circuit includes an accelerometer.

In certain examples, the sensing circuit 610, the control circuit 615, the detection circuit 620, and the memory 625 are included in a wearable device or a handheld device. In variations the memory 625 or a portion of the memory can be included in a separate device or can be a central memory located in a network "cloud."

The control circuit 615 may include a microprocessor, a digital signal processor, application specific integrated circuit (ASIC), or other type of processor, interpreting or executing instructions included in software or firmware. The memory 625 may be integral to or separate from the control circuit 615. The detection circuit 620 may also be integral to the control circuit 615 or may be separate from the control circuit 615. In certain examples, the sensing circuit 610 is included in a first device and the arrhythmia detection circuit and the control circuit are included in a second separate device. In certain examples, the first device is implantable and the second devices is external, such as the external device 412 of FIG. 4.

Ambulatory medical devices can be used to record cardiac events for analysis by a clinician. For instance, it may be desirable to use an ambulatory medical (e.g., a CFM device) to detect and record atrial fibrillation (AF) episodes of a patient, but the patient may not be prescribed a device that includes dedicated atrial sensing capability. Yet patients with these types of devices may develop atrial arrhythmias, such as AF. This is especially true for heart failure patients who typically have a high incidence of AF. A challenge is to record the onset portion of an AF episode. By the time the episode is detected by the device, the onset may have already passed and a recording of the onset is not available to the clinician.

As explained above, the sensing circuit 610 of FIG. 6 can include a cardiac signal sensing circuit. The sensing circuit may sample the cardiac signal sensing circuit. The control circuit 615 initiates the storing of sampled values of a segment of the sensed cardiac signal (e.g., an electrogram) in temporary memory storage. In some examples, sampled values obtained during an AF detection window are stored. The control circuit 615 may recurrently initiate the AF detection window according to a schedule or in response to another detected event.

Figure 7:
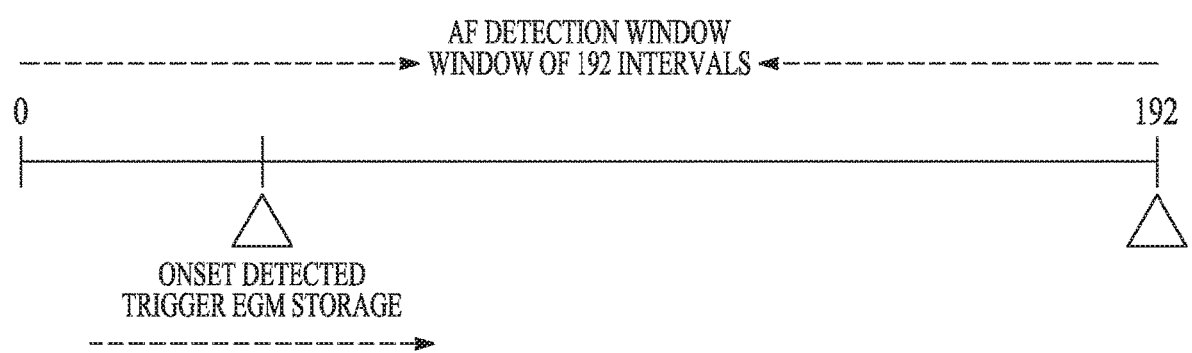
FIG. 7 illustrates an approach to triggering the storing of a physiological signal.

FIG. 7 is an example of an AF detection window. In the example, the AF detection window includes a number (e.g., 192) ventricular depolarization intervals and the temporary storage is a memory buffer sized to store sampled values collected over the intervals. The memory may be temporary storage because the control circuit 615 may initiate overwriting of the stored samples when the memory of the temporary storage becomes full.

The detection circuit 620 can detect onset of AF in a sensed cardiac signal using a first AF detection criterion and can confirm that the episode is AF using a second AF detection criterion. When the second AF detection criterion is satisfied, the detection circuit 620 provides an indication of AF confirmation to the control circuit 615. The indication may be a signal communicated to the control circuit 615. In response to receiving the indication that AF is confirmed, the control circuit 615 stores the sampled values in the non-temporary memory storage. The memory may be non-temporary because this memory is not subject to overwriting.

In certain examples, the temporary memory storage is an onset buffer 640 and the non-temporary storage is an event storage buffer 645. The control circuit 615 initiates transfer of the contents of the onset buffer to the event storage buffer in response to the indication that AF is confirmed. In some examples, the temporary memory storage is a first area of memory and the non-temporary storage is in a second area of memory, and the control circuit initiates transfer of the contents of the first area of memory to the second area of memory in response to the indication that AF is confirmed. In certain examples, the ambulatory medical device 605 includes a communication circuit (not shown) to communicate information to a separate device. The temporary memory may be located in the ambulatory medical device and the non-temporary memory may located in a network cloud. The control circuit 615 initiates transfer of the contents of the device memory to the cloud memory in response to the indication that AF is confirmed. In certain examples, the control circuit 615 stores the sampled in values in non-temporary storage by changing the designation of the memory from temporary to non-temporary, and does transfer the contents of memory from one memory location to another. For instance, the control circuit 615 may change the value of a pointer that is used to point to temporary memory. Changing the pointer prevents the stored contents from being overwritten.

As shown in the example of FIG. 7, because the triggering of storage of the cardiac signal is not dependent on the detection of the onset of AF, the onset portion of the AF episode is recorded. The recorded onset of AF can be used to make decisions for treatment of the subject. If a pause in AF is present during the onset of AF, pacing can be used to treat the AF. If atrial tachycardia is present during the onset of AF, then anti-tachy pacing can be used to treat the AF. If atrial flutter is present during the onset of AF, then atrial flutter ablation can be performed to treat AF of the subject.

In some examples, the detection circuit 620 provides an indication of AF onset to the control circuit 615 when the first AF detection criterion is satisfied, and the control circuit 615 stores the indication of AF onset in one or both of the temporary storage and the non-temporary storage in association with the sampled values of the segment of the cardiac signal. The first AF detection criterion may have greater sensitivity to AF detection than the second AF detection criterion, and the second AF detection criterion may have greater specificity to AF detection than the first AF detection criterion.

According to some examples, the first AF detection criterion used to detect onset of AF is a sudden change in heart rate of the subject. Using a sensed cardiac activity signal, the detection circuit 620 monitors information corresponding to ventricular depolarization (V-V) intervals. The detection circuit 620 detects AF onset when detecting a change in the V-V intervals that exceeds a specified a V-V interval change threshold. The threshold may be specified as a V-V interval change value that occurs within a specified period of time or a V-V interval that occurs in X of Y heart beats, where X and Y are integers and Y is greater than X. The detection circuit 620 generates the indication of AF onset in response to the change in the V-V intervals being detected. Alternatively, the sudden rate change can be detected as a change in heart rate (e.g., measured in beats per minute or bpm). The detection circuit 620 detects AF onset when detecting a change in heart rate that exceeds a specified rate change value that occurs within a specified period of time.

Figure 8:
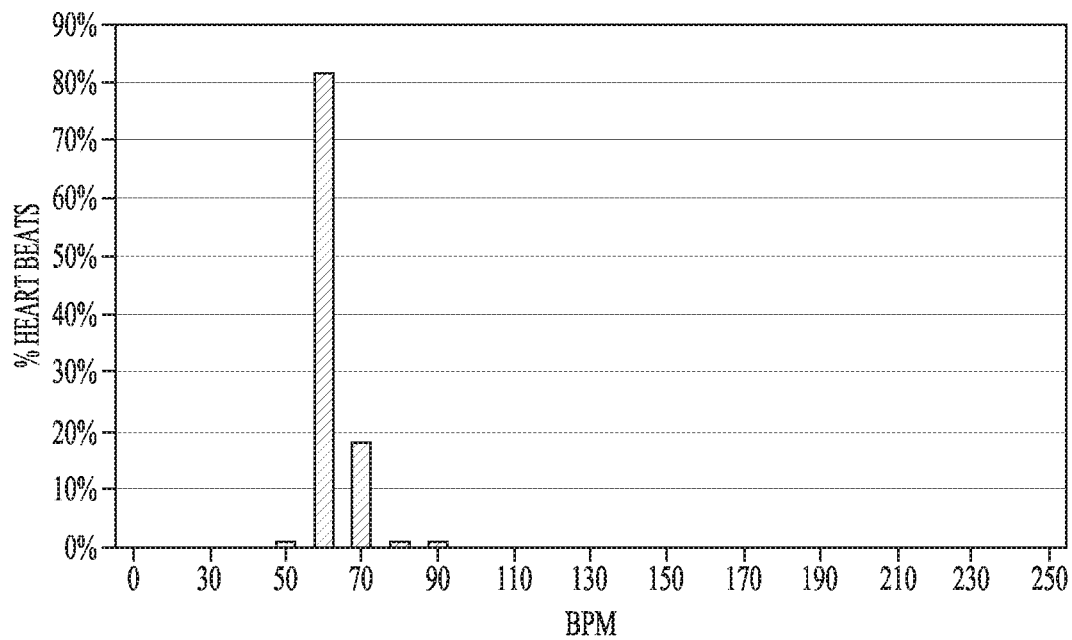
FIG. 8 shows a graph of an example of a heart rate distribution for normal sinus rhythm.

According to some examples, the first AF detection criterion uses a measure of heart rate mode to detect AF onset. FIG. 8 shows a graph of an example of a heart rate distribution for normal sinus rhythm (NSR). The horizontal axis is beats per minute and the vertical axis is percentage of the heart beat samples. Alternatively, the horizontal axis may show values of V-V intervals. Most of the samples of the distribution are located between approximately 50 bpm and 90 bpm. The heart rate mode is the heart rate having the most samples in the distribution, or the heart rate corresponding to a V-V interval value having the most samples in a V-V interval distribution. In the example of FIG. 8, the heart rate mode is 60 bpm.

Figure 9:
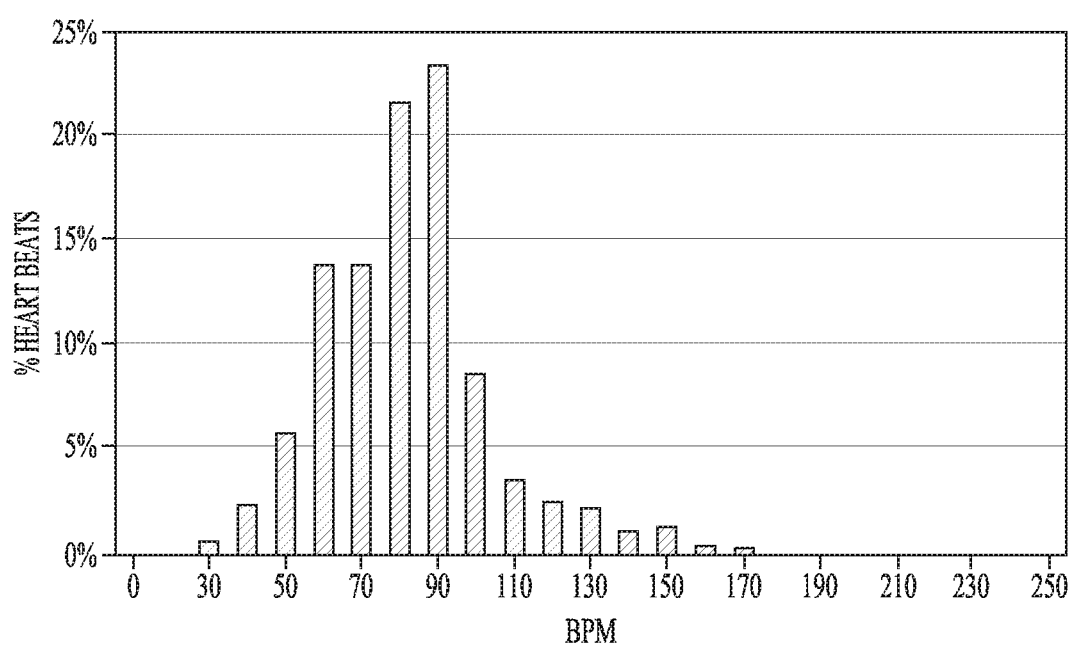
FIG. 9 shows a graph of an example of a heart rate distribution for a patient in atrial fibrillation.

FIG. 9 shows a graph of an example of a heart rate distribution for a patient in AF. It can be seen that heart rate is less regular in AF than for the example of NSR in FIG. 8. In the example of FIG. 9, the heart rate mode has shifted to 90 bpm. To detect onset of AF, the detection circuit 620 of FIG. 6 may determine a heart rate mode as the heart rate corresponding to a V-V interval value having the most samples in the V-V interval distribution, and compares the heart rate mode to a specified heart rate mode threshold value. The detection circuit 620 generates the indication of AF onset when the heart rate mode satisfies the specified heart rate mode threshold value.

Figure 10:
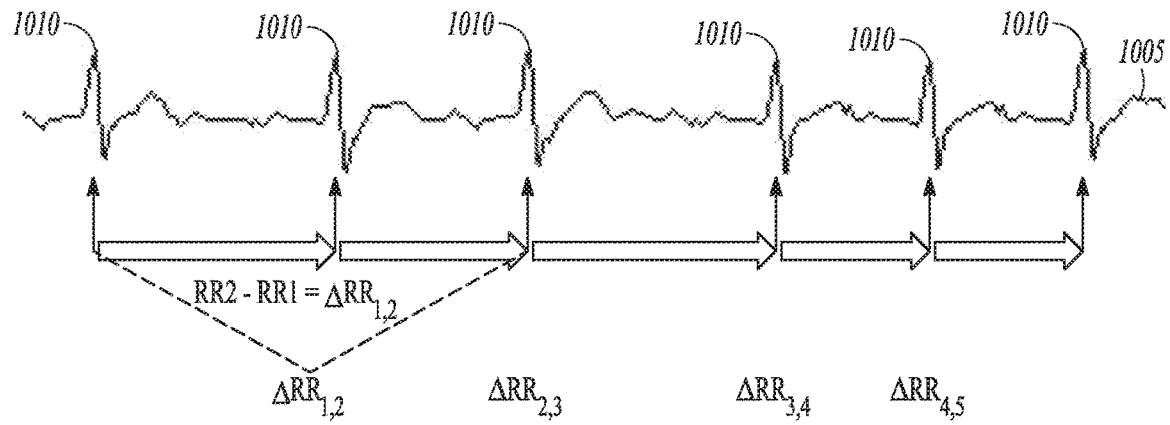
FIG. 10 shows a representation of a sensed cardiac signal.

According to some examples, the first AF detection criterion uses a measure of ventricular depolarization (V-V) interval dispersion or V-V interval scatter. FIG. 10 shows a representation of a sensed cardiac signal 1005. The signal is shown having a number of R-waves 1010. The V-V intervals can be determined as intervals between R-waves. RR1 in FIG. 10 refers to the first interval between the first two R-waves; RR2 is the second interval between the second R-wave and the third R-wave, and so on. Differences between the V-V intervals are referred to as $\Delta RR_{1,2}$ (e.g., the difference between the RR2 and RR1), $\Delta RR_{2,3}$, and so on.

Figure 11:
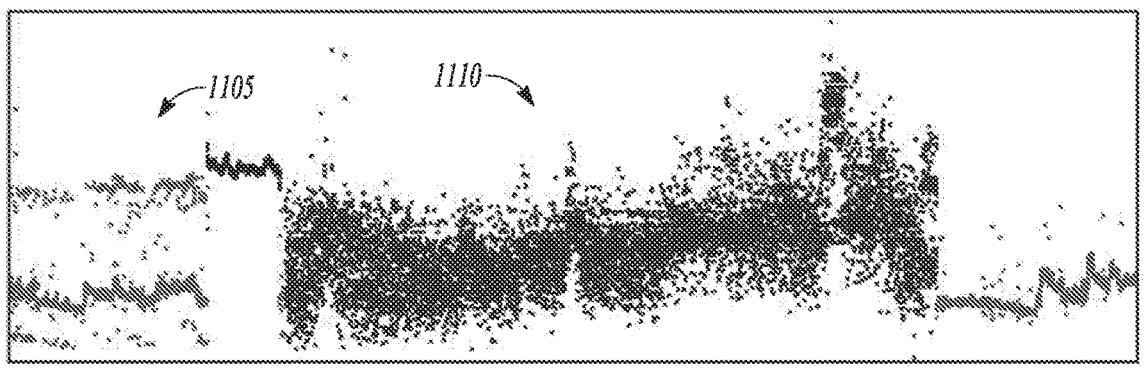
FIG. 11 is an example of a sensed physiological signal having a first region corresponding to normal sinus rhythm and a second region corresponding to atrial fibrillation.

FIG. 11 shows an example of a sensed physiological signal having a first region 1105 corresponding to NSR and a second region 1110 corresponding to AF. In the NSR region, the V-V intervals will be more regular and the differences in the V-V intervals will be small. In the AF region, the V-V intervals will be more scattered and the values of the differences in the V-V intervals will be more varied than for NSR.

In some examples, the detection circuit 620 of FIG. 6 may determine ventricular depolarization (V-V) intervals using the sensed physiological signal and monitors information corresponding to the V-V intervals. The detection circuit 620 may include a peak detector circuit to detect R-waves in the sensed physiological signal to determine V-V intervals. The detection circuit 620 may sample the V-V intervals and store the samples in device memory 625 or a different memory. The detection circuit 620 may determine differences between the V-V intervals and determine a measure of V-V interval dispersion using the determined V-V interval differences.

In some examples, the measure of V-V interval dispersion includes a determined variance of the determined interval differences. As the first AF detection criterion, the detection circuit 620 may compare the determined variance to a specified variance threshold value and generate an indication of AF onset when the determined variance satisfies the specified variance threshold value.

Other measures of ventricular interval dispersion can be used as the first AF detection criterion. In some examples, the detection circuit 620 determines the differences in the V-V intervals and classifies the interval differences as one of stable, unstable, or unstable and random. The interval classifications can be used to determine V-V interval dispersion.

In certain variations, the intervals are classified into a stable bin, an unstable bin, or an unstable-random bin. An interval difference may be classified as stable when the interval difference is less than a specified threshold difference value from an immediately previous interval difference. An interval difference may be classified as unstable when the interval difference is more than the specified threshold difference value from the immediately previous interval difference, and classified as unstable-random when the magnitude of the interval difference is more than the specified threshold difference value from the immediately previous interval difference and the interval difference is a negative value, that satisfies a specified negative value threshold.

In certain examples, the threshold difference value is a value corresponding to less than a 10 bpm difference in rate between the two intervals. Thus, if RR2 in FIG. 10 is 1000 ms corresponding to 60 bpm, and RR1 is 857 ms corresponding to 70 bpm, the interval difference $\Delta RR_{1,2}$ is binned as stable. If RR1 is less than 857 ms, then the interval difference is binned as unstable. If RR2 is less than 857 ms and RR1 is equal to 1000 ms, the interval difference $\Delta RR_{1,2}$ is binned as unstable-random. In certain examples, interval differences are only considered for binning if the intervals used (e.g., interval RR1 and RR2) are included in a triplet of three ventricular beats that are longer than a specified minimum interval (e.g., an interval of 324 ms corresponding to a heart rate of 185 bpm).

In the example of FIG. 11, more of the V-V interval differences will be stable in the NSR region. In the AF region, the number of unstable V-V interval differences and unstable-random V-V interval differences will increase relative to the number of stable V-V interval differences. The detection circuit 620 may determine a first metric of ventricular interval dispersion using a number of stable interval differences and a number of unstable interval differences. The first metric may include a first ratio determined using a number of stable interval differences and a number of unstable interval differences (e.g., first ratio=unstable/stable).

The detection circuit 620 may determine a second metric of ventricular interval dispersion using a determined portion of the interval differences that are unstable-random. The second metric may include a second ratio determined using a number of unstable-random interval differences and a sum including the number of stable interval differences and the number of unstable interval differences (e.g., second ratio= (unstable-random)/(stable+unstable)).

In the case where the first and second metrics are the ratios, the value of the first ratio will increase in the presence of AF because the number of V-V intervals classified as unstable will increase. The value of the second ratio will tend to increase in the presence of AF because the number of V-V intervals differences classified as unstable-random will increase.

As the first AF detection criterion, the arrhythmia detection circuit 620 may compare the determined first ratio to a specified first ratio threshold value (e.g., a ratio value of 3) and compare the determined second ratio to a specified second ratio threshold value (e.g., a ratio value of 0.06 or 6%). The detection circuit 620 generates the indication of AF onset when the first ratio satisfies the specified first ratio threshold value and the determined second ratio satisfies the specified second ratio threshold value.

To confirm that the detected onset is indeed AF, the detection circuit 620 uses a second AF detection criterion. In some examples the detection circuit 620 uses heart rate density index (HRDI) as the second AF detection criterion. The detection circuit 620 determines a V-V interval distribution using sampled V-V interval values and determines HRDI as a portion of the sampled V-V interval values corresponding to a V-V interval occurring most often in the distribution. (Alternatively, the HRDI corresponds to a heart rate occurring most often in a heart rate distribution.) In some variations, HRDI can be expressed as a fraction (e.g., a percentage) of the intervals. In the example of NSR of FIG. 9, the HRDI is 81% corresponding to the heart rate mode of 60 bpm. FIG. 10 shows a graph of an example of a heart rate distribution for a patient in AF. In the example of FIG. 10, the HRDI is approximately 23%. The detection circuit 620 compares the HRDI to a specified HRDI threshold value and generates an indication of AF when the determined HRDI satisfies the HRDI threshold value. In the examples of FIGS. 9-10, the detection circuit 620 may generate an indication of AF as the second AF detection criterion when the HRDI is less than 25%.

As explained previously, the first AF detection criterion may have greater sensitivity to AF detection than the second AF detection criterion, and the second AF detection criterion may have greater specificity to AF detection than the first AF detection criterion. The difference in sensitivity and specificity can be implemented by adjusting the thresholds of the first AF detection criterion and the second AF detection criterion. For instance, the specified V-V dispersion threshold value of the first AF detection criterion can be lowered to include more candidate rhythms as AF, and the HRDI of the second AF detection criterion can be lowered to make the second AF detection more difficult to satisfy.

Other methods of AF detection can be used for one or both of the first AF detection criterion and the second AF detection criterion. In some examples, the second AF detection criterion uses morphology of a sensed cardiac signal to confirm AF. The detection circuit 620 may calculate a score associated with correlation of the morphology of the sensed cardiac signal to the morphology of a template signal representative of AF. An example of a correlation score is a feature correlation coefficient (FCC). The FCC can provide an indication of a degree of similarity between the shape of the sensed electrogram and the shape of the template electrogram signal that represents AF. The template may be recorded for a particular subject or may be created based on a patient population. An approach to calculating a correlation score can be found in U.S. Pat. No. 7,904,142, titled "Self-Adjusting ECG Morphological Feature Correlation Threshold," filed May 16, 2007, which is incorporated herein by reference in its entirety. The detection circuit 620 may generate an indication of confirmation of AF when the calculated correlation score satisfies a specified threshold score. The detection for AF can be adjusted to be sensitive or less sensitive by adjusting the threshold score.

The physiological signal can include information of the hemodynamic system of the subject. During AF, the performance of the subject's hemodynamic system may be degraded. The degraded performance may be reflected in the physiological signal. The second AF detection criterion may confirm AF when detecting a degradation in hemodynamic function.

In some examples, the sensing circuit 610 includes a PAP sensing circuit that generates a PAP signal representative of PA of the subject. An episode of AF may result in a reduction in PAP of the subject reflected in the sensed PAP signal. The detection circuit 620 may apply the second AF detection criterion to the sensed PAP signal to confirm an AF detection using the first AF detection criterion. In certain examples, the second AF detection criterion generates an indication of AF confirmation when the PAP as reflected in the PAP signal decreases below a specified PAP threshold value.

The physiological signal used to confirm AF may be different than the physiological signal used to detect onset of AF. For instance, the first AF detection criterion may be applied to a sensed electrogram signal and the second AF detection criterion applied to a PAP signal. In some examples, the physiological signal used to confirm AF may be the same as the physiological signal used to detect onset of AF. For instance, the first AF detection criterion and the second AF detection criterion can both be applied to the sensed PAP signal, with the detection by the first criterion more sensitive than the detection by the second criterion.

In some examples, the sensing circuit 610 includes a heart sound sensing circuit that generates a heart sound signal representative of one or more heart sounds of the subject. An episode of AF may result in a change to a heart sound parameter measurable in the heart sound signal. For example, the amplitude of an S1 or S2 heart sound may decrease during an AF episode. In some examples, the arrhythmia detection circuit 620 applies the second AF detection criterion to the sensed heart sound signal to confirm an AF detection using the first AF detection criterion. The first AF detection criterion may be applied to a sensed electrogram signal as described previously herein or may be a criterion applied to the heart sound signal, with the detection by the first criterion more sensitive than the detection by the second criterion. In certain examples, the first AF detection criterion is applied to a different heart sound parameter than the second AF detection criterion.

In some examples, the detection circuit uses multiple AF detection windows. For instance, one window can be used to detect AF onset and a second window can be used to confirm AF. The control circuit 615 may initiate sensing of the cardiac signal during a first specified detection time duration as the first AF detection window using the first AF detection criterion. Sampled values of a cardiac activity signal sensed during the first detection window are stored in temporary storage. If AF onset is not detected, the memory of the temporary storage may be overwritten during the first AF detection window.

If AF onset is detected by the detection circuit 620 during the first AF detection window, the control circuit 615 initiates sensing of the cardiac signal during a second AF detection window. The detection circuit 620 applies the second AF detection criterion to the cardiac signal sensed during the second window to confirm AF. In some examples, the detection circuit 620 applies the second AF detection criterion to both the stored sampled values in the temporary memory storage and to the cardiac signal sensed in the second AF detection window to confirm AF.

If AF is confirmed, the control circuit 615 stores the sampled values sensed during the first detection window in non-temporary memory storage. The control circuit 615 may only store the segment sensed during the first AF detection window because this segment includes the onset of AF. The second segment is a continuation of the AF episode. If AF is not confirmed during the second AF detection window, the detection circuit 620 may revert to checking for AF onset. The detection circuit may re-initiate the first AF detection window if AF is not confirmed during the second AF detection window.

According to some examples, the ambulatory medical device includes a therapy circuit 650 for coupling to electrodes to provide an anti-arrhythmic cardiac therapy to a subject. The therapy circuit provides electrical anti-arrhythmia therapy to the subject. When AF is confirmed by the detection circuit 620, the control circuit 615 may initiate electrical pacing therapy or anti-tachy pacing therapy to treat the AF episode.

According to some examples, a patient with HF may experience syncope, yet it can be difficult to diagnose the cause of the syncope. It may be desirable to use the ambulatory medical device 605 to detect and record episodes of syncope for the patient. Implantable loop recorders (ILRs) can be used to detect the cause of undiagnosed syncope, but the cause can remain unexplained in a large portion of patients. ILRs often include a button for the patient to press when the patient experiences syncope. However, when syncope occurs, important information may be lost due to buffer overwriting by the time the subject recovers enough to press the button.

Figure 12:
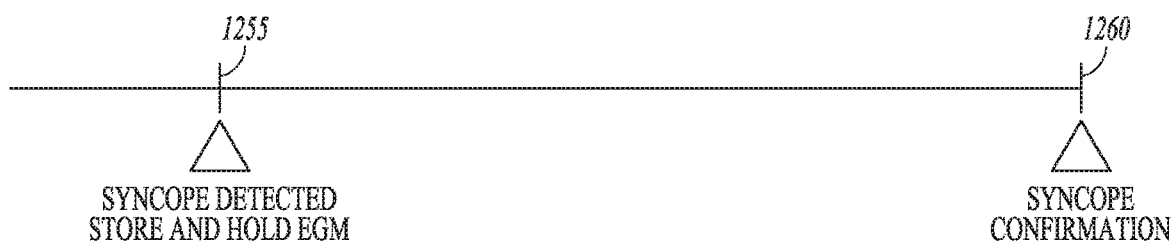
FIG. 12 illustrates an example triggering the storing of a cardiac signal in response to detection of syncope.

FIG. 12 is a diagram of an example of triggering electrogram storage in response to detecting a cardiac event such as syncope. Sensed physiological signals can include information useful to detect onset of syncope. In some examples, the detection circuit 620 of FIG. 6 detects onset of syncope using a sensed physiological signal at 1255 of FIG. 12. The sensing circuit 610 generates a sensed cardiac activity signal and may generate one or more other types of sensed physiological signals. In response to the detection of onset of syncope, the control circuit 615 triggers storage of the sampled values of a segment of a sensed cardiac activity signal in temporary memory storage in response to detection of syncope. At 1260, the control circuit 616 initiates storage of the sampled values in non-temporary storage in response to receiving an indication of confirmation of syncope. The confirmation may be an indication (e.g., a message) received from a separate device that the patient or subject confirms syncope, or the confirmation may be an indication (e.g., a signal) received from the detection circuit 620 that may confirm syncope using one or more of the sensed physiological signals.

The detection circuit 620 may determine heart rate using a sensed cardiac activity signal and may detect onset of syncope of the subject using the determined heart rate. In some examples, the detection circuit detects syncope when detecting a sudden increase in heart rate. In some examples, the detection circuit 620 detects syncope when detecting pauses in heart beats of the subject. The detection circuit 620 sends on indication of syncope to the control circuit 615 and the control circuit 615 initiates storage of sampled values of the sensed cardiac activity signal. In some examples, the detection circuit determines ventricular depolarization rate during syncope using the sensed cardiac activity signal, and stores determined ventricular depolarization rates in the non-temporary storage as a histogram.

In some examples, the sensing circuit 610 generates a sensed hemodynamic signal representative of hemodynamic information of the subject in addition to the cardiac activity signal. Some examples of a hemodynamic signal include a signal representative of respiration of the subject, a signal representative of blood pressure of the subject, and a signal representative of one or more heart sounds of the subject.

The detection circuit 620 may detect syncope of the subject using the hemodynamic signal. For instance, in certain examples the detection circuit 620 may detect syncope from a pause in breathing or a reduction in breathing volume. In certain examples, the detection circuit 620 may detect syncope when detecting that blood pressure of the subject decreases below a specified threshold value of blood pressure. In certain examples, the detection circuit 620 may detect syncope when detecting a decrease in the amplitude of a heart sound (e.g., a decrease in S2) in a sensed heart sound signal that satisfies a specified threshold value of heart sound amplitude.

In some examples, the sensing circuit 610 includes a posture sensing circuit and the detection circuit 620 detects syncope using a sensed posture signal that include posture information of the subject. For instance, the detection circuit 620 may detect syncope when the subject undergoes a sudden change in posture from upright to supine. In some examples, the sensing circuit includes a physical activity sensor and the detection circuit 620 detects syncope using a detected posture change and a detected reduction in physical activity.

The ambulatory medical device 605 may confirm syncope using one or more of the sensed physiological signals. The detection circuit 620 may use a first syncope detection criterion that is very sensitive to syncope detection and may use a second syncope detection criterion that is more specific to syncope detection. For instance, the detection circuit 620 may use heart rate information for the first syncope detection criterion and use other hemodynamic information for the second syncope detection criterion. In response to confirming syncope, the sensed electrogram is stored in non-temporary storage.

According to some examples, the ambulatory medical device 605 receives confirmation of syncope from a second device, such as external device 412 in FIG. 4. The ambulatory medical device 605 can include a communication circuit 635 to communicate information wirelessly with a second device which includes a second communication circuit and may include a user interface. When the detection circuit 620 detects syncope the ambulatory medical device 605 communicates an indication to the second device. The second device presents a prompt to the subject to confirm syncope using the user interface. The ambulatory medical device 605 may send frequent communications or alerts to the second device until a confirmation of syncope or an indication of no syncope is returned. If the user confirms syncope, the second device initiates communication of the indication of confirmation of syncope or indication of no syncope to the first device. The ambulatory medical device stores the sensed electrogram in non-temporary memory in response to receiving a confirmation of syncope from the second device.

In some examples, the detection circuit 620 detects ventricular tachycardia (VT). The control circuit 615 may adjust a VT detection parameter of the detection circuit in response to the confirmation of syncope. For instance, if syncope is confirmed or confirmed a threshold number of times, the control circuit 615 may adjust the parameter to be more sensitive to VT detection.

The devices, methods and systems described herein provide device-recorded information related to cardiac events experienced by the patient. These recorded episodes include recording of the onset of the event. The recording can be uploaded from the device and evaluated by a clinician. The recorded onset of a physiological condition of the patient can lead to improved treatment of the patient's condition and more effective device-based therapy provided to the patient.

ADDITIONAL DESCRIPTION AND EXAMPLES

Example 1 can include subject matter (such as an apparatus) comprising a sensing circuit configured to generate a sensed physiological signal, wherein the physiological signal includes physiological information of a subject; a detection circuit electrically coupled to the sensing circuit and configured to detect a physiological condition of a subject using the physiological signal; and a control circuit configured to store sampled values of a segment of the physiological signal in temporary memory storage; and to store the sampled values in non-temporary storage in response to receiving an indication of continued detection of the physiological condition.

In Example 2, the subject matter of Example 1 optionally includes a control circuit configured to trigger storage of the sampled values of the segment of the physiological signal in temporary memory storage in response to detection of onset of the physiological condition; and to store the sampled values in non-temporary storage in response to receiving an indication of confirmation of the physiological condition as the indication of continued detection of the physiological condition.

In Example 3, the subject matter of one or both of Examples 1 and 2 optionally includes a detection circuit configured to detect syncope of the subject, and wherein the control circuit is configured to trigger storage of the sampled values in temporary memory storage in response to detection of syncope of the subject; and to store the sampled values in non-temporary storage in response to receiving an indication of confirmation of syncope of the subject.

In Example 4, the subject matter of Example 3 optionally includes a sensing circuit configured to generate a sensed hemodynamic signal representative of hemodynamic information of the subject, and wherein the detection circuit is configured to detect syncope of the subject using the hemodynamic signal.

In Example 5, the subject matter of Example 4 optionally includes a sensing circuit configured to generate a sensed hemodynamic signal representative of at least one of respiration of the subject, blood pressure of the subject, one or more heart sounds of the subject.

In Example 6, the subject matter of one or any combination of Examples 3-5 optionally includes a sensing circuit configured to generate one or both of a sensed posture signal representative of posture of the subject and a sensed activity signal representative of patient activity, and wherein the detection circuit is configured to detect syncope of the subject using one or both of the posture signal and the activity signal.

In Example 7, the subject matter of one or any combination of Examples 3-6 optionally includes a sensing circuit configured to generate a sensed cardiac signal representative of electrical cardiac activity of the subject, and wherein the detection circuit is configured to determine heart rate using the cardiac activity signal and detect syncope of the subject using the determined heart rate.

In Example 8, the subject matter of one or any combination of Examples 3-7 optionally includes a sensing circuit configured to generate a sensed cardiac signal representative of electrical cardiac activity of the subject, wherein the detection circuit is configured to determine ventricular depolarization rate during syncope using the sensed cardiac signal, and to store determined ventricular depolarization rates in the non-temporary storage as a histogram.

In Example 9, the subject matter of one or any combination of Examples 1-8 optionally includes a sensing circuit configured to generate a sensed cardiac signal representative of electrical cardiac activity of a subject; wherein the detection circuit is configured to: detect onset of atrial fibrillation (AF) in the sensed cardiac signal as the physiological condition using a first AF detection criterion; confirm the AF using a second AF detection criterion, wherein the first AF detection criterion has greater sensitivity to AF detection than the second AF detection criterion, and the second AF detection criterion has greater specificity to AF detection than the first AF detection criterion; and provide an indication of AF confirmation to the control circuit as the indication of continued detection; and wherein the control circuit is configured to: recurrently store the sampled values of the segment of the cardiac signal in the temporary memory storage; and store the sampled values in the non-temporary memory storage in response to receiving the indication of AF confirmation.

In Example 10, the subject matter of Example 9 optionally includes a detection circuit configured to: monitor information corresponding to ventricular depolarization (V-V) intervals; determine a V-V interval distribution using sampled V-V interval values; and wherein the detection circuit, according to the second AF detection criterion, is further configured to: determine a heart rate density index (HRDI) as a portion of the sampled V-V interval values corresponding to a V-V interval occurring most often in the distribution; compare the HRDI to a specified HRDI threshold value; and generate the indication of AF confirmation when the determined HRDI satisfies the HRDI threshold value.

In Example 11, the subject matter of one or both of Examples 9 and 10 optionally includes a physiological sensing circuit configured to generate a physiological signal that includes physiological information of the subject, wherein the detection circuit is configured to confirm the AF by applying the second AF detection criterion to the sensed physiological signal.

In Example 12, the subject matter of Example 11 optionally includes a physiological sensing circuit that includes at least one of a heart sound sensor circuit and a pulmonary arterial pressure sensor circuit.

In Example 13, the subject matter of one or any combination of Examples 9-12 optionally includes a detection circuit configured to provide an indication of AF onset to the control circuit, and wherein the control circuit is configured to store the indication of AF onset in one or both of the temporary storage and the non-temporary storage in association with the sampled values of the segment of the cardiac signal.

In Example 14, the subject matter of one or any combination of Examples 9-13 optionally includes a detection circuit configured to (according to the first AF detection criterion): determine a heart rate mode as the heart rate corresponding to a V-V interval value having most samples in the V-V interval distribution; compare the heart rate mode to a specified heart rate mode threshold value; and generate the indication of AF onset when the heart rate mode satisfies the specified heart rate mode threshold value.

In Example 15, the subject matter of one or any combination of Examples 9-13 optionally includes a detection circuit configured to (according to the first AF detection criterion): monitor information corresponding to ventricular depolarization (V-V) intervals; detect a change in the V-V intervals that exceeds a specified a V-V interval change threshold; and generate the indication of AF onset in response to the change in the V-V intervals being detected.

In Example 16, the subject matter of one or any combination of Examples 9-15 optionally includes a memory including a first onset buffer and a second event storage buffer, and wherein the control circuit is optionally configured to: store sampled values of the sensed cardiac signal in the onset buffer and overwrite sampled values previously stored in the onset buffer; and initiate, in response to the AF detection by the first and second AF detection criterion, storing of the sampled values stored in the onset buffer in the event storage and storing subsequently sampled values of the sensed cardiac signal in the event storage buffer.

Example 17 can include subject matter (such as a medical device system), or can optionally be combined with the subject matter of one or any combination of Examples 1-16 to include such subject matter, comprising a first device that includes: a sensing circuit configured to generate a sensed physiological signal, wherein the physiological signal includes physiological information of a subject; a detection circuit electrically coupled to the sensing circuit and configured to detect onset of syncope of the subject using the physiological signal; a first communication circuit electrically coupled to the control circuit and configured to communicate wireless signals with a separate device, including to receive an indication of confirmation of syncope from the separate device; and a control circuit electrically coupled to the syncope detection circuit and the control circuit, wherein the control circuit is configured to: trigger storage of sampled values of a segment of the physiological signal in temporary memory storage in response to detection of onset of syncope; and to store the sampled values in non-temporary storage in response to receiving an indication of confirmation of syncope.

In Example 18, the subject matter of Example 17 optionally includes a second device comprising: a second communication circuit configured to communicate wireless signals with the first device; a user interface; a control circuit electrically coupled to the communication circuit and the user interface, wherein the control circuit is configured to: present a prompt to the subject to confirm syncope; and initiate communication of the indication of confirmation of syncope to the first device in response to receiving a confirmation of syncope via the user interface.

Example 19 can include subject matter (such as an apparatus), or can optionally be combined with the subject matter of one or any combination of Examples 1-18 to include such subject matter, comprising a sensing circuit is configured to generate a sensed cardiac signal representative of cardiac activity of a subject; a control circuit; and an arrhythmia detection circuit configured to: detect onset of atrial fibrillation (AF) in the sensed cardiac signal using a first AF detection criterion; confirm AF using a second AF detection criterion, wherein the first AF detection criterion has greater sensitivity to AF detection than the second AF detection criterion, and the second AF detection criterion has greater specificity to AF detection than the first AF detection criterion; and provide an indication of AF confirmation to the control circuit; and wherein the control circuit is configured to: initiate sensing of the cardiac signal during a first specified detection time duration as a first AF detection window using the first AF detection criterion; store sampled values of the sensed cardiac signal sensed during the first detection window in temporary storage; recurrently overwrite memory of the temporary storage during the first detection window; initiate, in response to detection of onset of AF during the first AF detection window, sensing of the cardiac signal during a second AF detection window using the second AF detection criterion and the stored sampled values in the temporary memory storage; and store the sampled values of the cardiac signal sensed during the first detection window in non-temporary memory storage in response to confirming AF using the second AF detection criterion.

In Example 20, the subject matter of Example 19 optionally includes a therapy circuit electrically coupled to the control circuit and configured for coupling to electrodes to provide an anti-arrhythmic cardiac therapy to a subject, and wherein the control circuit is configured to initiate delivery of an anti-arrhythmic pacing therapy in response to the generated indication of confirmation of AF.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

These non-limiting examples can be combined in any permutation or combination.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like. In some examples, a carrier medium can carry code implementing the methods. The term "carrier medium" can be used to represent carrier waves on which code is transmitted.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
 a sensing circuit configured to generate a sensed physiological signal, wherein the physiological signal includes ventricular depolarization (V-V) interval information of a subject;
 a detection circuit electrically coupled to the sensing circuit and configured to:
  during a detection window, detect a cardiac arrhythmia of a subject using a V-V interval stability detection criterion; and
  at the end of the detection window, confirm the cardiac arrhythmia using a second detection criterion more specific than the V-V interval stability detection criterion, wherein the V-V interval stability detection criterion is more sensitive than the second detection criterion; and
 a control circuit configured to:
  store, in response to detection of cardiac arrhythmia using the V-V interval stability, sampled values of a segment of the physiological signal during the detection window in temporary memory storage;
  receive, after detection of the cardiac arrhythmia using the V-V interval stability, an indication of confirmation of the detected cardiac arrhythmia using the second detection criterion; and
  store, in response to receiving the indication of confirmation of the detected cardiac arrhythmia, the sampled values of the segment of the physiological signal during the detection window in non-temporary storage.

2. The apparatus of claim 1, wherein the control circuit is configured to confirm the cardiac arrhythmia using the sampled values of the segment of the physiological signal stored in the temporary memory storage in response to detection of onset of the cardiac arrhythmia; and to store the sampled values in the non-temporary storage in response to receiving the indication of confirmation of the detected cardiac arrhythmia.

3. The apparatus of claim 2, wherein the detection circuit is configured to detect syncope of the subject, and wherein the control circuit is configured to trigger storage of the sampled values in temporary memory storage in response to detection of syncope of the subject; and to store the sampled values in non-temporary storage in response to receiving an indication of confirmation of syncope of the subject.

4. The apparatus of claim 3, wherein the sensing circuit is configured to generate a sensed hemodynamic signal representative of hemodynamic information of the subject, and wherein the detection circuit is configured to detect syncope of the subject using the hemodynamic signal.

5. The apparatus of claim 4, wherein the sensing circuit is configured to generate a sensed hemodynamic signal representative of at least one of respiration of the subject, blood pressure of the subject, one or more heart sounds of the subject.

6. The apparatus of claim 3, wherein the sensing circuit is configured to generate one or both of a sensed posture signal representative of posture of the subject and a sensed activity signal representative of patient activity, and wherein the detection circuit is configured to detect syncope of the subject using one or both of the posture signal and the activity signal.

7. The apparatus of claim 3, wherein the sensing circuit is configured to generate a sensed cardiac signal representative of electrical cardiac activity of the subject, and wherein the detection circuit is configured to determine heart rate using the cardiac activity signal and detect syncope of the subject using the determined heart rate.

8. The apparatus of claim 3, wherein the sensing circuit is configured to generate a sensed cardiac signal representative of electrical cardiac activity of the subject, wherein the detection circuit is configured to determine ventricular depolarization rate during syncope using the sensed cardiac signal, and to store determined ventricular depolarization rates in the non-temporary storage as a histogram.

9. The apparatus of claim 1,
 wherein the sensing circuit is configured to generate a sensed cardiac signal representative of electrical cardiac activity of a subject;
 wherein the detection circuit is configured to:
  detect onset of atrial fibrillation (AF) in the sensed cardiac signal using the V-V interval stability detection criterion as a first AF detection criterion;
  confirm the AF using the second detection criterion as a second AF detection criterion, wherein the first AF detection criterion has greater sensitivity to AF detection than the second AF detection criterion, and the second AF detection criterion has greater specificity to AF detection than the first AF detection criterion; and
  provide an indication of AF confirmation to the control circuit; and
 wherein the control circuit is configured to:
  recurrently store the sampled values of the segment of the cardiac signal in the temporary memory storage; and
  store the sampled values in the non-temporary memory storage in response to receiving the indication of confirmation of AF.

10. The apparatus of claim 9, wherein the detection circuit is configured to:
 determine a V-V interval distribution using sampled V-V interval values; and
 wherein the detection circuit, according to the second AF detection criterion, is further configured to:
  determine a heart rate density index (HRDI) as a portion of the sampled V-V interval values corresponding to a V-V interval occurring most often in the distribution;
  compare the HRDI to a specified HRDI threshold value; and
  generate the indication of AF confirmation when the determined HRDI satisfies the HRDI threshold value.

11. The apparatus of claim 9, including a physiological sensing circuit configured to generate a physiological signal that includes physiological information of the subject, wherein the detection circuit is configured to confirm the AF by applying the second AF detection criterion to the sensed physiological signal.

12. The apparatus of claim 11, wherein the physiological sensing circuit includes at least one of a heart sound sensor circuit and a pulmonary arterial pressure sensor circuit.

13. The apparatus of claim 9, wherein the detection circuit is configured to provide an indication of AF onset to the control circuit in response to the detection of AF onset using the first AF detection criterion, and wherein the control circuit is configured to store the indication of AF onset in one or both of the temporary storage and the non-temporary storage in association with the sampled values of the segment of the cardiac signal.

14. The apparatus of claim 13, wherein the detection circuit, according to the first AF detection criterion, is configured to:
determine a heart rate mode as the heart rate corresponding to a V-V interval value having most samples in the V-V interval distribution;
compare the heart rate mode to a specified heart rate mode threshold value; and
generate the indication of AF onset when the heart rate mode satisfies the specified heart rate mode threshold value.

15. The apparatus of claim 14, wherein the detection circuit, according to the first AF detection criterion, is configured to:
monitor information corresponding to ventricular depolarization (V-V) intervals;
detect a change in the V-V intervals that exceeds a specified a V-V interval change threshold; and
generate the indication of AF onset in response to the change in the V-V intervals being detected.

16. The apparatus of claim 9, wherein the memory includes a first onset buffer and a second event storage buffer, and wherein the control circuit is configured to: store sampled values of the sensed cardiac signal in the onset buffer and overwrite sampled values previously stored in the onset buffer; and initiate, in response to the AF detection by the first and second AF detection criterion, storing of the sampled values stored in the onset buffer in the event storage and storing subsequently sampled values of the sensed cardiac signal in the event storage buffer.

17. The apparatus of claim 1, wherein the sampled values of the segment of the physiologic signal include an electrocardiogram.

18. An apparatus comprising:
a sensing circuit is configured to generate a sensed cardiac signal representative of cardiac activity of a subject;
a control circuit; and
an arrhythmia detection circuit configured to:
detect atrial fibrillation (AF) in the sensed cardiac signal using a first AF detection criterion that includes V-V interval stability;
confirm AF using a second AF detection criterion, wherein the first AF detection criterion has greater sensitivity to AF detection than the second AF detection criterion, and the second AF detection criterion has greater specificity to AF detection than the first AF detection criterion; and
provide an indication of AF confirmation to the control circuit; and
wherein the control circuit is configured to:
initiate sensing of the cardiac signal during a first specified detection time duration as a first AF detection window using the first AF detection criterion;
store sampled values of the sensed cardiac signal sensed during the first detection window in temporary storage;
recurrently overwrite memory of the temporary storage during the first detection window;
initiate, in response to detection of AF during the first AF detection window, sensing of the cardiac signal during a second AF detection window using the second AF detection criterion and the stored sampled values in the temporary memory storage, wherein the second AF detection window has a longer time duration than the first AF detection window; and
store the sampled values of the cardiac signal sensed during the first AF detection window in non-temporary memory storage in response to confirming AF using the second AF detection criterion.

19. The apparatus of claim 18, including a therapy circuit electrically coupled to the control circuit and configured for coupling to electrodes to provide an anti-arrhythmic cardiac therapy to a subject, and wherein the control circuit is configured to initiate delivery of an anti-arrhythmic pacing therapy in response to the generated indication of confirmation of AF.

* * * * *